United States Patent [19]

Wolfram

[11] Patent Number: 4,481,369
[45] Date of Patent: Nov. 6, 1984

[54] PREPARATION OF α-KETO-CARBOXYLIC ACIDS FROM ACYL HALIDES

[75] Inventor: Joachim W. Wolfram, Baton Rouge, La.

[73] Assignee: Ethyl Corporation, Richmond, Va.

[21] Appl. No.: 518,022

[22] Filed: Jul. 28, 1983

[51] Int. Cl.³ .............................................. C07C 51/10
[52] U.S. Cl. ..................................... 562/406; 562/517
[58] Field of Search ................................ 562/406, 517

[56] References Cited

U.S. PATENT DOCUMENTS 3,923,880 12/1975 Westlake et al. .................... 562/517
3,946,082 3/1976 McVicker ........................... 562/577
3,980,702 9/1976 Grinstead ............................ 562/577
4,372,889 2/1983 Rizkalla .

FOREIGN PATENT DOCUMENTS 2026478 2/1980 United Kingdom ................ 562/406

OTHER PUBLICATIONS

Saegusa et al, Journal of Organic Chem., vol. 42, No. 16, 2797–2798, (1977).
Tachibona et al, Chem. Letters, pp. 1765–1768, (1982).

Primary Examiner—Paul J. Killos
Attorney, Agent, or Firm—Donald L. Johnson; John F. Sieberth; John F. Hunt

[57] ABSTRACT

A process for the production of α-keto-carboxylic acids of the general formula:

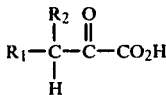

wherein $R_1$ and $R_2$ are the same or different and are hydrogen, hydrocarbyl radicals, substituted hydrocarbyl radicals or hydrocarbyloxy radicals by reacting an acyl halide of the formula:

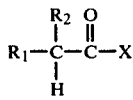

wherein $R_1$ and $R_2$ are as defined above and X represents halogen, in a liquid solvent medium, with an alkali metal tricarbonyl[triphenylphosphine]cobaltate complex of the formula:

$MCo(CO)_3Ph_3$ wherein M is an alkali metal to form the corresponding phenylacetyl tricarbonyl[triphenylphosphine]cobalt complex of the formula:

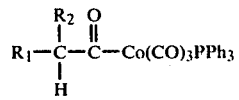

wherein $R_1$ and $R_2$ are as defined above, reacting the acylcobaltcarbonyl complex thus formed with carbon monoxide and an alkali metal hydroxide or an alkaline earth metal hydroxide at elevated temperature and elevated pressure in a liquid solvent medium to form the corresponding alkali metal salt or alkaline earth metal salt of the product α-keto-carboxylic acid and thereafter acidifying the salt of the α-keto-carboxylic acid to form the product α-keto-carboxylic acid.

18 Claims, No Drawings

PREPARATION OF α-KETO-CARBOXYLIC ACIDS FROM ACYL HALIDES

BACKGROUND

The present invention relates to a process for the carbonylation of an acyl halide to form an α-keto-carboxylic acid as the product.

The practical value of such α-keto-carboxylic acids is that they can be used to prepare the corresponding α-amino-acids or α-hydroxy acids which play an important role in biochemistry. For example, Saegusa et al, *Journal of Organic Chemistry*, Vol. 42, No. 16, 2797-2798 (1977) teach the selective reduction of α-keto acids to α-hydroxy acids by the use of certain phosphites as reducing agents. And, Tachibana et al, *Chemistry Letters*, pp. 1765-1768 (1982) disclose the transformation of α-keto acids to the corresponding α-amino acids by the reaction with chiral pyridoxamine analog, (R)- or (S)-15-aminomethyl-14-hydroxy-5,5-dimethyl-2,8-dithia[9](2,5)pyridinophane (4), and $Zn^{2+}$ in the molar ratio of 2:1, in methanol.

The preparation of α-keto-carboxylic acids and their derivatives has been the subject of a large number of investigations. According to Rodd, *The Chemistry of Carbon Compounds* (1952 edition), Vol. 1, pages 227-229, the following methods of preparation are available:

gentle oxidation of α-hydroxyacids containing a secondary hydroxyl group, or by the enzymatic deamination of α-amino-acids;

hydrolysis of an acyl cyanide;

hydrolysis of α-oximino-esters;

from glycidic acid esters on treatment with benzene saturated with boron trifluoride;

from α,β-dibromocarboxylic acids by forming a piperidine addition compound followed by hydrolysis;

from α-keto-acetals by ultraviolet irradiation in the presence of N-bromosuccinimide;

from α-bromomethylketones by boiling with selenium dioxide in absolute methanol or ethanol;

from carboxylic acid esters by oxidation with selenium dioxide;

permanganate oxidation of vinyl ketones;

from carboxylic acid esters by condensation with oxalic ester followed by decarboxylation;

from aldehydes via 5-alkylidine-2-thio-oxazolid-4-ones or by reaction with methyl methoxyacetate; hydrolysis of azalactones or acetamido-acrylic acids; hydrolysis of the reaction product of Grignard reagents on diethyl-oxamic ester;

oxidation of -hydroxyacid esters containing two β-hydrogen atoms by N-bromosuccinimide in carbon tetrachloride to β-bromo-α-keto-acid esters; and by the action of alpha on the dimethanesulphonates and ditoluene-p-sulphonates of α,β-dihydroxycarboxylic acids.

In pending U.S. Ser. No. 353,473, entitled "Process for Preparing Alkyl Alpha-Keto-Carboxylic Acids from Alkyl Halides", filed on Mar. 1, 1982, there is disclosed a method of preparing an alkyl α-keto-carboxylic acid by reacting a primary alkyl halide in a liquid solvent medium with carbon monoxide at elevated temperature and elevated pressure in the presence of a catalytic amount of a metal carbonyl compound, such as dicobalt-octacarbonyl and an alkali metal base or an alkaline earth metal base.

Methods also are known for preparing arylpyruvic acids. For example, U.S. Pat. No. 4,152,352 discloses the preparation of an arylpyruvic acid by reacting an arylmethyl halide in a liquid solvent medium with carbon monoxide at pressures of 5 to 200 bars in the presence of a catalytic amount of a metal carbonyl compound and an alkaline earth metal inorganic base. Further, U.K. patent application No. 2,026,478A discloses that alkali metal salts of an arylpyruvic acid can be prepared by reacting an arylmethyl halide, carbon monoxide and an alkali metal base in the presence of a metal carbonyl compound as catalyst and in the presence of an alcohol or cyclic ether as solvent.

Finally, it is known in the art to react an acyl halide or alkyl halide in the presence of carbon monoxide, with a nucleophilic transition metal anionic complex to produce the corresponding acyl metal carbonyl derivative. See, for example, Heck, *Organotransition Metal Chemistry*, (Academic Press, New York, N.Y. 1974) pp. 200-209.

SUMMARY

It has now been found that α-keto-carboxylic acids of the general formula:

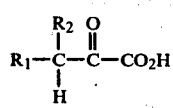

in which $R_1$ and $R_2$ are the same or different and represent hydrogen, a hydrocarbyl radical, a substituted hydrocarbyl radical or a hydrocarbyloxy radical, can be prepared by carbonylating an acyl halide of the formula:

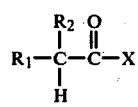

wherein $R_1$ and $R_2$ are as defined above and X represents halogen, in a liquid solvent medium, with an alkali metal tricarbonyl[triphenylphosphine]cobaltate complex of the formula:

wherein M is an alkali metal, to form the corresponding phenylacetyl tricarbonyl[triphenylphosphine]cobalt complex of the formula:

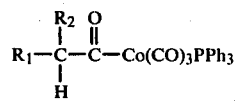

wherein $R_1$ and $R_2$ are as defined above, reacting the phenylacetyl tricarbonyl[triphenylphosphine]cobalt complex thus formed with carbon monoxide and an alkali metal hydroxide or an alkaline earth metal hydroxide at elevated temperature and elevated pressure in a liquid solvent medium to form the corresponding alkali metal salt or alkaline earth metal salt of the product α-keto-carboxylic acid and thereafter acidifying the salt of the product α-keto-carboxylic acid to form the resultant α-keto-carboxylic acid. By this method, acyl halides are readily and inexpensively converted to α-keto-carboxylic acids.

THE INVENTION

The α-keto-carboxylic acids of the present invention are compounds having the general formula:

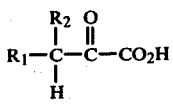

$$R_1-\underset{\underset{H}{|}}{\overset{\overset{R_2}{|}}{C}}-\overset{\overset{O}{\|}}{C}-CO_2H$$

wherein $R_1$ and $R_2$ are the same or different and are selected from hydrogen, hydrocarbyl radicals, substituted hydrocarbyl radicals and hydrocarbyloxy radicals. Preferably, the hydrocarbyl radicals are those that contain up to about 20 carbon atoms. For purposes of this invention a hydrocarbyl radical can be defined as an organic group solely composed of hydrogen and carbon atoms. Some non-limiting representative examples of hydrocarbyl radicals are alkyl, cycloalkyl, alkenyl, aralkyl, alkaryl, and aryl.

Examples of suitable alkyl groups are methyl, ethyl, n-propyl, isopropyl, n-butyl, isobutyl, sec-butyl, tert-butyl, n-amyl, and the various positional isomers thereof, and likewise the corresponding straight and branched chain isomers of hexyl, heptyl, octyl, nonyl, decyl, undecyl, dodecyl, and the like.

Some examples of cycloalkyl groups are cyclopropyl, cyclobutyl, cyclopentyl, cyclohexyl, cycloheptyl, cyclooctyl, cyclononyl, cyclodecyl, cycloundecyl, cyclododecyl, and the like. They may also be such cycloaliphatic groups as α-cyclopropyl-ethyl, α-cyclobutyl-propyl, β-cyclobutyl-propyl, and similar alkyl derivatives of the higher cycloalkyls.

Some examples of alkenyl groups are ethenyl, 1-propenyl, 2-propenyl, isopropenyl, 1-butenyl, 2-butenyl, 3-butenyl, and the corresponding branched-chain isomers thereof as for example, 1-isobutenyl, 2-isobutenyl, 2-sec-butenyl, including 1-methylene-2-propenyl, and the various isomers of pentenyl, hexenyl, heptenyl, octenyl, nonenyl, decenyl, undecenyl, and dodecenyl, including 3,3-dimethyl-1-butenyl, 2,3-dimethyl-1-butenyl, 2,3-dimethyl-2-butenyl, 2,3-dimethyl-3-butenyl, 1-methyl-1-ethyl-2-propenyl, and the like.

Examples of alkaryl groups are tolyl, 2,3-xylyl, 2,4-xylyl, 2,5-xylyl, 2,6-xylyl, 3,4-xylyl, 3,5-xylyl; o, m, and p-cumenyl, mesityl, o, m, and p-ethylphenyl, 2-methyl-1-naphthyl, 3-methyl-1-naphthyl, 4-methyl-1-naphthyl, 5-methyl-2-naphthyl, 6-methyl-3-naphthyl, 7-methyl-1-naphthyl, 8-methyl-4-naphthyl, 1-ethyl-2-naphthyl, and its various positional isomers and the like.

Examples of aryl groups which may be present in the above general formula are phenyl, naphthyl, and the like.

Examples of aralkyl groups are benzyl, phenylethyl, 1-phenylpropyl, 2-phenylpropyl, 3-phenylpropyl, 1- and 2-isomers of phenylisopropyl, 1-, 2-, and 3-isomers of phenylbutyl, and the like.

The substituted hydrocarbyl radicals are hydrocarbyl radicals which contain substituents such as halogen, carboxyl, or amide radicals.

As mentioned above, the hydrocarbyl groups may be halogen substituted. Thus, chlorine, bromine, iodine, and fluorine may be substituted on the alkyl, cycloalkyl, alkenyl, alkaryl, aryl, and aralkyl groups which are present. Non-limiting examples of such substituted groups are chloromethyl, chloroethyl, bromoethyl, 2-fluoro-1,2-dibromoethyl, 1-iodopropyl, 2-fluoropropyl, 1-chlorobutyl, 2-bromobutyl, 2-iodo-2-methylpropyl, 1-chloropentyl, 3-fluoro-2-methylbutyl, 3-iodo-2-methylbutyl, 1-chloro-2,2-dimethylpropyl, 2-chloroheptyl, 3-fluorononyl, 1-chlorododecyl, and the like. Examples of halogenated cycloalkyl groups are chlorocyclopropyl, chlorocyclohexyl, 1,2-dichlorohexyl, bromocyclobutyl, iodocyclohexyl, and the like.

Examples of halogen-substituted alkenyl groups are bromoethenyl, chloroethenyl, iodoethenyl, 1-bromododecenyl, and the like.

Examples of halogenated alkaryl groups are chloro-o-tolyl, chloro-p-tolyl, chloro-m-tolyl, 2-bromo-3,4-xylyl, 4-bromo-2,3-xylyl, 5-bromo-2,4-xylyl, 2-bromo-4,5-xylyl, o-, m-, and p-tolyl, 3-bromomesityl, chloro(4-methyl)-1-naphthyl, iodo(ethyl)-1-naphthyl, all positional isomers of the above, and the like.

Examples of halogen substituted aryl groups are bromophenyl, 2-bromo-1-naphthyl, 3-bromo-1-naphthyl and all positional isomers thereof, 2,4-dibromophenyl, 2,3-dibromophenyl, 2,5-dibromophenyl, 2,3,4,5-tetrabromophenyl, 2,3,5,6-tetrabromophenyl, pentabromophenyl, all isomers of chlorophenyl, and all isomers of multichlorophenyl: 2-chloro-1-naphthyl and the remaining isomers thereof: 2,3-dichloro-1-naphthyl, 2,4-dichloro-1-naphthyl and the remaining positional isomers of dichloronaphthyl, 2,3,4,5-tetrachloro-1-naphthyl.

The hydrocarbyl groups may contain amide groups which may be illustrated by such non-limiting examples as: carbamoylmethyl, 2-carbamoylethyl, 4-carbamoylbutyl, 8-carbamoyl-2-ethyloctyl, 1,4-dicarbamoylbutyl, carbamoylcyclopentyl, carbamoylcyclohexyl, 2-carbamoyl-o-tolyl, 2-carbamoyl-m-tolyl, 3-carbamoyl-p-tolyl, (carbamoylmethyl)phenyl, (2-carbamoylethyl)benzyl: o-, m-, and p-(carbamoylethyl)phenyl, and the like.

Representative examples of α-keto-carboxylic acids which can be made by the process of the present invention include:
pyruvic acid,
2-oxo-butanoic acid
2-oxo-3-methylbutyric acid,
2-oxo-dodecanoic acid,
cyclohexylglyoxylic acid,
2-oxo-hept-6-enoic acid,
phenylpyruvic acid,
p-tolylpyruvic acid,
benzylpyruvic acid,
2-chloro-2-oxopropinoic acid,
p-chlorophenylpyruvic acid, and the like.

Acyl halides suitable for use in the present process are those halides having the structural formula:

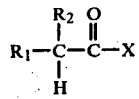

$$R_1-\underset{\underset{H}{|}}{\overset{\overset{R_2}{|}}{C}}-\overset{\overset{O}{\|}}{C}-X$$

wherein $R_1$ and $R_2$ are the same or different and are hydrogen, hydrocarbyl radicals, substituted hydrocarbyl radicals or hydrocarbyloxy radicals, as defined above, and X is halogen. Primarily, acyl halides having from 1 to about 20 atoms are preferred. Acylfluorides and acyliodides may be used, but it is preferable to use acylhalides of the "middle halogens"—i.e., acylchlorides and acylbromides.

Methods for preparing acyl halides are well known. For example, acyl halides are prepared by the substitution of a halide radical for the hydroxyl radical of a carboxylic acid. Three reagents are commonly used for this purpose: thionyl chloride, $SOCl_2$; phosphorus trichloride, $PCl_3$; and phosphorous pentachloride, $PCl_5$. Thionyl chloride is particularly convenient, since the products formed besides the acid chloride are gases and thus are easily separated from the acid chloride. See, for example, Morrison and Boyd, *Organic Chemistry* (Allyn and Bacon, Inc., Boston, Mass., 1970), p. 601.

Representative examples of acyl halide reactants which can be used in the instant process include:
acetyl chloride,
acetyl bromide,
propanoyl chloride,
propanoyl bromide,
isobutyryl chloride,
isobutyryl bromide,
undecanoyl chloride
undecanoyl bromide,
cyclohexanecarbonyl chloride,
cyclohexanecarbonyl bromide,
hex-5-enoylchloride,
hex-5-enoylbromide,
phenylacetyl chloride,
phenylacetyl bromide,
p-tolylacetyl chloride,
p-tolylacetyl bromide,
3-phenylpropanoyl chloride,
3-phenylpropanoyl bromide,
chloroacetyl chloride
p-chlorophenylacetyl chloride, and the like.

The alkali metal tricarbonyl triphenyophosphino cobaltate complex of the invention is characterized by the following formula:

$$MCo(CO)_3PPh_3$$

wherein M is an alkali metal preferably selected from lithium, sodium, and potassium. The alkali metal tricarbonyl triphenylphosphino cobaltate reactant is readily prepared by reducing cobalt tricarbonyl triphenylphosphino dimer with a suitable reducing agent such as potassium hydride, sodium hydride or sodium amalgam in a solvent such as tetrahydrofuran to form the alkali metal tricarbonyl[triphenylphosphine]cobaltate.

The reaction between the acyl halide reactant of the invention and the alkali metal tricarbonyl[triphenylphosphine]cobaltate reactant is conveniently carried out at a reaction temperature of from about 0° C. up to about 50° C., with a temperature range of from about 10° C. up to about 30° C. being preferred, at ambient pressure, in the presence of a suitable reaction solvent.

Solvents which may be used in the reacton are those solvents which are inert under the reaction conditions. That is, the reaction is carried out in the presence of a solvent which does not enter into the reaction. Aprotic solvents which include ethers such as diethyl ether, dibutyl ether, 1-ethoxyhexane, tetrahydrofuran, 1,4-dioxane, 1,3-dioxolane, diglyme, 1,1-diethoxyethane, and tertiary amines such as pyridine, N-ethylpiperidine, triethylamine, tributylamine, N,N-diphenyl-N-methylamine, N,N-dimethylalanine, etc. can be used in the practice of the process. Also, dipolar aprotic solvents such as dimethyl sulfoxide, N,N-dimethylformamide, N,N-dimethylacetamide, dimethyl sulfone, tetramethylene sulfone, N-methylpyrrolidine, acetonitrile and like materials can be used in the process. Other solvents which are inert under the reaction conditions may be used: for example, low boiling hydrocarbons, halogenated hydrocarbons, examples of which are benzene, toluene, tetrachloroethane, the chlorinated benzenes, the chlorinated toluenes and the like.

In general, equimolar amounts of the alkali metal tricarbonyl[triphenylphosphine]cobaltate complex and the acyl halide reactant are used in the reaction.

The reaction is readily conducted by placing the acyl halide and the cobaltate complex in a suitable reaction vessel having agitation means. The process is preferably conducted in a substantially anhydrous reaction system and, accordingly, the components of the reaction system should be brought together and maintained under a substantially dry, inert atmosphere. Thus, while it is possible to conduct this process in the presence of moisture, it is desirable to maintain the reaction system under an atmosphere of dry nitrogen or the like.

The mode of addition is not particularly critical. Accordingly, it is convenient to add the acyl halide reactant to a mixture of the other materials, add the alkali metal tricarbonyl[triphenylphosphine]cobaltate complex to a mixture of the other materials, introduce all ingredients simultaneously into the reaction zone or the like.

The reaction of the acyl halide component and the cobaltate complex yields a phenylacetyl tricarbonyl triphenyl complex of the formula:

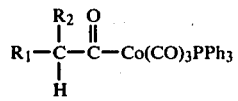

wherein the $R_1$ and $R_2$ substituents are derived from and are the same as those substituents contained in the acyl halide reactant.

The phenylacetyl tricarbonyl[triphenylphosphine]cobalt complex once formed is subsequently reacted with carbon monoxide and an alkali metal hydroxide or an alkaline earth metal hydroxide at elevated temperature and elevated pressure to form the corresponding alkali metal salt or alkaline earth metal salt of the product α-keto-carboxylic acid. An absence of basic reagent in the process prevents the formation of the desired α-keto-carboxylic acid.

Specific examples of alkali metal hydroxides and alkaline earth metal hydroxides which can be used in the practice of the process include: LiOH, NaOH, KOH, RbOH, $Ca(OH)_2$, $Ba(OH)_2$ and $Mg(OH)_2$. Calcium hydroxide is particularly preferred.

The amount of basic agent used in the process can vary within wide limits. In general, the molar ratio of the alkali metal hydroxide or alkaline earth metal hydroxide to the phenylacetyl tricarbonyl[triphenylphosphine]cobalt complex is preferably 1:1 to 10:1.

The reacton of the phenylacetyl tricarbonyl[triphenylphosphine]cobalt complex, basic reagent and carbon monoxide is carried out in the presence of a mixture of water and a suitable reaction solvent which is inert under the reaction conditions. Suitable solvents include the aforementioned aprotic solvents such as ethers, including diethyl ether, dibutyl ether, 1-ethoxyhexane, tetrahydrofuran, 1,4-dioxane, 1,3-dioxolane, diglyme, 1,1-diethoxyethane, tertiary amines such as pyridine, N-ethylpiperidine, triethylamine, tributylamine, N,N-diphenyl-N-methylamine, N,N-dimethylalanine, and the like. Also, the aforementioned dipolar aprotic solvents such as dimethyl sulfoxide, N,N-dimethylformamide, N,N-dimethylacetamide, dimethyl sulfone, tetramethylene sulfone, N-methylpyrrolidine, acetonitrile and like materials can be used in the reaction. Other solvents, for example, low boiling hydrocarbons, halogenated hydrocarbons, examples of which are benzene, toluene, tetrachloroethane, the chlorinated benzenes, the chlorinated toluenes and the like also may be used in the reaction. A particularly preferred solvent is tetrahydrofuran and a particularly preferred solvent system is water and tetrahydrofuran. Mixtures containing from about 10% to 90% by weight of water and from about 90% to 10% by weight tetrahydrofuran can be used. Typically, a solvent mixture containing about 90% by weight tetrahydrofuran and 10% by weight water is used as the solvent system.

The reaction between the phenylacetyl tricarbonyl[triphenylphosphine]cobalt complex, the alkali metal hydroxide or alkaline earth metal hydroxide reactant and carbon monoxide is advantageously carried out by bringing the mixture consisting of the complex and basic agent suspended in a mixture of water and solvent into contact, under nitrogen, in a suitable pressure-resistant reactor equipped with a stirrer, with a large excess of carbon monoxide (i.e., amounts greater than 2 moles of carbon monoxide per mole of the phenylacetyl tricarbonyl triphenylphosphino cobaltate complex) introduced at the desired pressure and temperature, in accordance with techniques suitable for bringing about the reaction between a liquid phase and a gas phase.

The carbonylation reaction is carried out at a temperature in the range of from about 30° C. to about 150° C., preferably from about 50° C. to about 100° C., over a period of time of from about 1 to 20 hours.

In general, the reaction takes place at elevated carbon monoxide pressures which may range from about 300 psig to about 3000 psig. Preferably, the reaction takes place at a pressure in the range of about 800 psig to 1000 psig. The carbon monoxide may contain or be mixed with an inert gas, such as nitrogen.

Upon completion of the reaction, the product mixture is filtered, if necessary, as when $Ca(OH)_2$ is used as the basic reagent, resulting in the alkali metal salt or the alkaline earth metal salt of the desired α-keto-carboxylic acid being separated from the liquid rection component as the main solid component which is thereafter acidified to form the product α-keto-carboxylic acid. The filtrate contains the remainder of the alkali metal salt or alkaline earth metal salt of the α-keto-carboxylic acid in addition to unreacted phenylacetyl tricarbonyl[triphenylphosphine]cobalt complex and the corresponding carboxylic acid. In some instances, a solid alkali metal salt or an alkaline earth metal salt does not form and instead remains in solution when certain basic reagents other than calcium hydroxide are used. In such cases, the salt is acidified in solution.

The metal salt of the α-keto-carboxylic acid is acidified with a dilute acid, such as hydrochloric acid, sulfuric acid, or nitric acid, so as to displace the α-keto-carboxylic acid from its alkali metal salt or its alkaline earth metal salt. The solution obtained is extracted with a suitable solvent, for example, an ether such as diethyl ether, and the organic extract thus obtained is purified by conventional acid-base workup. The final residue consists of the product α-keto-carboxylic acid and the corresponding carboxylic acid derived from the acyl halide reactant. The carboxylic acid can be recycled and transformed into starting acyl halide reactant by substitution of a halide radical for the hydroxyl radical of the carboxylic acid by the use of thionyl halide, phosphorous trihalide or phosphorous pentahalide as previously discussed.

If desired, esters of the α-keto-carboxylic acid products of the present invention can be prepared by esterifying the α-keto-carboxylic acid product according to conventional esterification techniques employing alcohols and acid catalysts such as, for example, $BF_3$, $BF_3.HCl$, $BF_3.MeOH$, $BF_3.Et_2O$ or diazomethane at suitable reaction conditions.

The following examples will illustrate the invention.

EXAMPLE I

Preparation of Potassium Tricarbonyltriphenylphosphino Cobaltate

A 250 mL three-neck round bottom flask in a dry box was charged with 8.0 g of 35% potassium hydrdride/oil dispersion. The flask was transferred to the hood, placed under nitrogen, and the potassium hydride was washed free of oil with dry tetrahydrofuran (3×10 mLs). The potassium hydride was suspended in 110 mLs of tetrahydrofuran in a flask and 10.0 g of cobalt tricarbonyl triphosphine dimer was added to the flask via a solid addition funnel under nitrogen. The reaction mixture was stirred overnight at room temperature. Analysis by IR indicated a concentration of 0.2 mmoles of potassium tricarbonyl [triphenylphosphine] cobaltate per mL of tetrahydrofuran.

EXAMPLE II

Preparation of Phenylpyruvic Acid

A 20 mL aliquot of 4.0 mmoles of potassium tricarbonyl [triphenylphosphine] cobaltate was charged to a 100 mL three-neck round bottom flask under nitrogen and cooled to 5° C. Phenylacetyl chloride (0.53 mL; 4 mmoles) was added to the flask, and the resultant solution containing the preformed cobaltate complex was charged into a 300 mL autoclave by means of a transfer needle under nitrogen. The autoclave had previously been charged with 16 mmoles (1.18 g) of calcium hydroxide as a suspension in 25 mLs tetrahydrofuran and 5 mLs water. The vessel was sealed, flushed with carbon monoxide, pressurized to 900 psig and heated to 50° C. for nine hours. The autoclave was vented and the contents were poured into a 250 mL separatory funnel. The reaction mixture was acidified with 10% hydrochloric acid and then treated with an excess of iodine. The organic phase was diluted with 100 mLs of diethyl ether and the lower aqueous phase was discarded. The organic phase was washed with saturated sodium thiosulfate until the color of iodine was dispelled. The resultant light yellow diethyl ether phase was washed with 10% sodium hydroxide (3×25 mLs) and the organic phase discarded. Acidification of the combined aqueous sodium hydroxide solution followed by re-extraction with diethyl ether (2×75 mLs) gave a clear solution. The solution was dried over $MgSO_4$ and evaporated to give (0.81 mmoles; 20.3% yield) of phenylpyruvic acid and 2.84 mmoles (71.1% yield) of phenylacetic acid as identified by mass spectroscopy and comparison to an authentic sample.

EXAMPLE III

Preparation of Phenylpyruvic Acid

The procedure of Example II was repeated except that reaction temperture was 90° C. All other reactants and conditions were the same. Phenylpyruvic acid (1.1 mmoles; 26.7% yield) and phenylacetic acid (2.54 mmoles; 63% yield) was obtained.

EXAMPLE IV

Preparation of Phenylpyruvic Acid

A 22.5 mL aliquot of 4.5 mmoles of potassium tricarbonyl [triphenylphosphine] cobaltate was charged to a 100 mL three-neck round bottom flask under nitrogen and cooled to 5° C. Phenylacetyl chloride (0.60 mL; 4.5 mmoles) was added to the flask. The solution containing the preformed cobaltate complex was then charged into a 300 mL autoclave by means of a transfer needle under nitrogen. The autoclave had previously been charged with 18.1 mmoles (3.1 g) of barium hydroxide as a suspension in 22.5 mLs tetrahydrofuran and 5 mLs water. The vessel was sealed, flushed with carbon monoxide, pressurized to 900 psig and heated to 90° C. for nine hours. The autoclave was vented and the contents were poured into a 250 mL separatory funnel. The reaction mixture was acidified with 10% hydrochloric acid and then treated with an excess of iodine. The organic phase was diluted with 100 mLs of diethyl ether and the lower aqueous phase was discarded. The organic phase was washed with saturated sodium thiosulfate until the color of iodine was dispelled. The resultant light yellow diethyl ether phase was washed with 10% sodium hydroxide (3×25 mLs) and the organic phase discarded. Acidification of the combined aqueous sodium hydroxide solution followed by re-extraction with diethyl ether (2×75 mLs) gave a clear solution. The solution was dried over MgSO4 and evaporated to give 0.07 mmoles (1.5% yield) of phenylpyruvic acid and 3.91 mmoles (86.8% yield) of phenylacetic acid as identified by mass spectroscopy and comparison to an authentic sample.

EXAMPLE V

Preparation of Phenylpyruvic Acid

A 20 mL aliquot of 0.15 mmoles/mL of potassium tricarbonyl [triphenylphosphine] cobaltate was charged to a 100 mL three-neck round bottom flask under nitrogen and cooled to 5° C. Phenylacetyl chloride (0.4 mL; 3.0 mmoles) was added to the flask. The solution containing the preformed cobaltate complex was then charged into a 300 mL autoclave by means of a transfer needle under nitrogen. The autoclave had previously been charged with 12 mmoles (0.287 g) of lithium hydroxide as a suspension in 22.5 mLs tetrahydrofuran and 5 mLs water. The vessel was sealed, flushed with carbon monoxide, pressurized to 900 psig and heated to 90° C. for nine hours. The autoclave was vented and the contents were poured into a 250 mL separatory funnel. The reaction mixture was acidified with 10% hydrochloric acid and then treated with an excess of iodine. The organic phase was diluted with 100 mLs of diethyl ether and the lower aqueous phase was discarded. The organic phase was washed with saturated sodium thiosulfate until the color of iodine was dispelled. The resultant light yellow diethyl ether phase was washed with 10% sodium hydroxide (3×25 mLs) and the organic phase discarded. Acidification of the combined aqueous sodium hydroxide solution followed by re-extraction with diethyl ether (2×75 mLs) gave a clear solution. The solution was dried over MgSO4 and evaporated to give 0.02 mmoles (0.76% yield) of phenylpyruvic acid and 2.18 mmoles (72.6% yield) of phenylacetic acid as identified by mass spectroscopy and comparison to an authentic sample.

Having described the process which Applicant regards as his invention, it should be recognized that changes and variations within the scope and spirit of the invention can be made by one skilled in the art and it is accordingly to be understood that the present description of the invention is illustrative only. It is desired that the invention be limited only by the lawful scope of the following claims.

I claim:

1. A method of preparing α-keto-carboxylic acids which comprises the steps of (i) reacting an acyl halide in a liquid solvent medium with an alkali metal tricarbonyl[triphenylphosphine]cobaltate complex to form the corresponding phenylacetyl tricarbonyl[triphenylphosphine]cobalt complex, (ii) reacting said phenylacetyl tricarbonyl[triphenylphosphine]cobalt complex with carbon monoxide and an alkali metal hydroxide or an alkaline earth metal hydroxide at elevated temperature and elevated pressure in a liquid solvent medium to form the corresponding alkali metal salt or alkaline earth metal salt of said α-keto-carboxylic acid, and (iii) thereafter acidifying said salt of said α-keto-carboxylic acid to form said α-keto-carboxylic acid.

2. A method of preparing α-keto-carboxylic acids of the general formula:

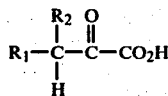

wherein R1 and R2 are the same or different and are hydrogen, hydrocarbyl radicals, substituted hydrocarbyl radicals or hydrocarbyloxy radicals which comprise the steps of (i) reacting an acyl halide of the general formula:

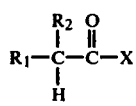

wherein R1 and R2 are as defined above and X represents halogen, in a liquid solvent medium, with an alkali metal tricarbonyl[triphenylphosphine]cobaltate complex of the formula:

wherein M is an alkali metal to form the corresponding phenylacetyl tricarbonyl[triphenylphosphine]cobalt complex of the general formula:

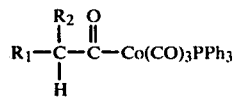

wherein R1 and R2 are as defined above, (ii) reacting the phenylacetyl tricarbonyl[triphenylphosphine]cobalt complex thus formed with carbon monoxide and an alkali metal hydroxide or an alkaline earth metal hydroxide at elevated temperature and elevated pressure in a liquid solvent medium to form the corresponding alkali metal salt or alkaline earth metal salt of said α-keto-carboxylic acid, and (iii) thereafter acidifying the salt of said α-keto-carboxylic acid to form said α-keto-carboxylic acid.

3. The method of claim 2 wherein $R_1$ and $R_2$ are the same or different and are hydrogen or a hydrocarbyl radical having up to 20 carbon atoms.

4. The method of claim 3 wherein $R_1$ and $R_2$ are the same or different and are hydrogen or a hydrocarbyl radical selected from alkyl, cycloalkyl, alkenyl, aralkyl, alkaryl and aryl.

5. The method of claim 4 wherein $R_1$ and $R_2$ are selected from hydrogen, methyl, ethyl, n-propyl, isopropyl, n-butyl, isobutyl, sec-butyl, tertiary butyl, n-amyl, hexyl, heptyl, octyl, nonyl, decyl, undecyl, dodecyl, cyclopropyl, cyclobutyl, cyclopentyl, ethenyl, 1-propenyl, tolyl, benzyl, and phenyl.

6. The method of claim 2 wherein X is chlorine, bromine, iodine and fluorine.

7. The method of claim 2 wherein M is lithium, sodium or potassium.

8. The method of claim 2 wherein said alkali metal hydroxide is lithium hydroxide, sodium hydroxide or potassium hydroxide.

9. The method of claim 2 wherein said alkaline earth metal hydroxide is magnesium hydroxide, calcium hydroxide or barium hydroxide.

10. The method of claim 2 wherein said acyl halide is acetyl chloride, acetyl bromide, propanoyl chloride, propanoyl bromide, isobutyryl chloride, isobutyryl bromide, undecanoyl chloride, undecanoyl bromide, cyclohexanecarbonyl chloride, cyclohexanecarbonyl bromide, hex-5-enoylchloride, hex-5-enoylbromide, phenylacetyl chloride, phenylacetyl bromide, p-tolylacetyl chloride, p-tolylacetyl bromide, 3-phenylpropanoyl chloride, 3-phenylpropanoyl bromide, chloroacetyl chloride, or p-chlorophenylacetyl chloride.

11. The method of claim 2 wherein said α-keto-carboxylic acid is pyruvic acid, 2-oxo-butanoic acid, 2-oxo-3-methylbutyric acid, 2-oxo-dodecanoic acid, cyclohexylglyoxylic acid, 2-oxo-hept-6-enoic acid, phenylpyruvic acid, p-tolylpyruvic acid, benzylpyruvic acid, 2-chloro-2-oxopropinoic acid, or p-chlorophenylpyruvic acid.

12. The method of claim 2 wherein the liquid solvent medium in step (i) is an aprotic solvent.

13. The method of claim 12 wherein said solvent is diethyl ether, dibutyl ether, 1-ethoxyhexane, tetrahydrofuran, 1,4-dioxane, 1,3-dioxolane, diglyme, 1,1-diethoxyethane, pyridine, N-ethylpiperidine, triethylamine, tributylamine, N,N-diphenyl-N-methylamine, N,N-dimethylalanine, dimethyl sulfoxide, N,N-dimethylformamide, N,N-dimethylacetamide, dimethyl sulfone, tetramethylene sulfone, N-methylpyrrolidine, or acetonitrile.

14. The method of claim 2 wherein the liquid solvent medium in step (ii) is a mixture of water and an aprotic solvent.

15. The method of claim 14 wherein said aprotic solvent is diethyl ether, dibutyl ether, 1-ethoxyhexane, tetrahydrofuran, 1,4-dioxane, 1,3-dioxolane, diglyme, 1,1-diethoxyethane, pyridine, N-ethylpiperidine, triethylamine, tributylamine, N,N-diphenyl-N-methylamine, N,N-dimethylalanine, dimethyl sulfoxide, N,N-dimethylformamide, N,N-dimethylacetamide, dimethyl sulfone, tetramethylene sulfone, N-methylpyrrolidine, or acetonitrile.

16. The method of claim 14 wherein the mixture consists of from about 10% to about 90% by weight water and from about 90% to about 10% by weight aprotic solvent.

17. The method of claim 2 wherein step (i) is carried out at a temperature of from abut 0° C. to about 50° C.

18. The method of claim 2 wherein step (ii) is carried out at a temperature of from about 30° C. up to about 150° C. and a pressure of from about 300 psig up to about 3000 psig.

* * * * *